US010687851B2

(12) United States Patent
Beijens et al.

(10) Patent No.: US 10,687,851 B2
(45) Date of Patent: Jun. 23, 2020

(54) TREATMENT HEAD FOR PERFORMING A MICRODERMABRASION PROCEDURE

(71) Applicant: KONINKLIJKE PHILIPS N.V., Eindhoven (NL)

(72) Inventors: Linda Goverdina Maria Beijens, Eindhoven (NL); Martin Jurna, Eindhoven (NL); Willem Verkruijsse, Eindhoven (NL); Hendrik Halling Van Amerongen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 44 days.

(21) Appl. No.: 15/513,174

(22) PCT Filed: Sep. 25, 2015

(86) PCT No.: PCT/EP2015/072159
§ 371 (c)(1),
(2) Date: Mar. 22, 2017

(87) PCT Pub. No.: WO2016/046391
PCT Pub. Date: Mar. 31, 2016

(65) Prior Publication Data
US 2018/0014855 A1      Jan. 18, 2018

(30) Foreign Application Priority Data

Sep. 25, 2014    (EP) .................................... 14186332

(51) Int. Cl.
*A61B 17/54*     (2006.01)
*A61B 17/00*     (2006.01)
*A61B 17/30*     (2006.01)

(52) U.S. Cl.
CPC .... *A61B 17/54* (2013.01); *A61B 2017/00734* (2013.01); *A61B 2017/306* (2013.01); *A61B 2217/005* (2013.01); *A61B 2217/007* (2013.01)

(58) Field of Classification Search
CPC .......... A61B 17/54; A61B 2017/00734; A61B 2017/306; A61B 2217/005
See application file for complete search history.

(56) References Cited

U.S. PATENT DOCUMENTS 5,836,311 A  *  11/1998  Borst ..................... A61B 17/02
                                                         128/897
6,193,589 B1     2/2001   Khalaj
                         (Continued)

FOREIGN PATENT DOCUMENTS

| JP | 1997095564 U | 7/1977 |
| JP | 1997098835 A | 4/1997 |
| JP | 3131031 U | 4/2007 |

*Primary Examiner* — Kathleen S Holwerda
*Assistant Examiner* — Brooke Labranche

(57) ABSTRACT

The present application relates to a treatment head (30) for performing a microdermabrasion procedure on a subject's skin (40). The treatment head (30) has a skin contact surface (32) which is positionable against the subject's skin (40) and at least one vacuum aperture (50) at the skin contact surface (32). The at least one vacuum aperture (50) defines a path (52) at which a vacuum is generatable. The at least one vacuum aperture (50) has an abrasive edge (56) defined by a juncture of the vacuum aperture and the skin contact surface. The abrasive edge is configured to act on the subject's skin (40). The present application also relates to a skin care device (10) for performing a microdermabrasion procedure on a subject's skin (40).

25 Claims, 4 Drawing Sheets

(56) References Cited

U.S. PATENT DOCUMENTS

| | | | | |
|---|---|---|---|---|
| 6,241,739 B1 * | 6/2001 | Waldron | ................. | A61B 17/54 |
| | | | | 606/131 |
| 6,299,620 B1 * | 10/2001 | Shadduck | .............. | A61B 17/54 |
| | | | | 604/289 |
| 6,464,629 B1 * | 10/2002 | Boone | .................... | A61B 17/02 |
| | | | | 600/37 |
| 6,500,183 B1 | 12/2002 | Waldron | | |
| 6,629,983 B1 | 10/2003 | Ignon | | |
| 6,641,591 B1 | 11/2003 | Shadduck | | |
| 6,926,681 B1 | 8/2005 | Ramey | | |
| 8,048,089 B2 | 11/2011 | Ignon | | |
| 2007/0225732 A1 | 9/2007 | Cho | | |
| 2010/0119836 A1 * | 5/2010 | Naritomi | ................. | B32B 15/08 |
| | | | | 428/416 |
| 2011/0082415 A1 * | 4/2011 | Ignon | .................... | A61B 17/54 |
| | | | | 604/22 |
| 2016/0106468 A1 | 4/2016 | Jansen | | |
| 2016/0157703 A1 * | 6/2016 | Brooks | .............. | A61B 1/00094 |
| | | | | 600/104 |

* cited by examiner

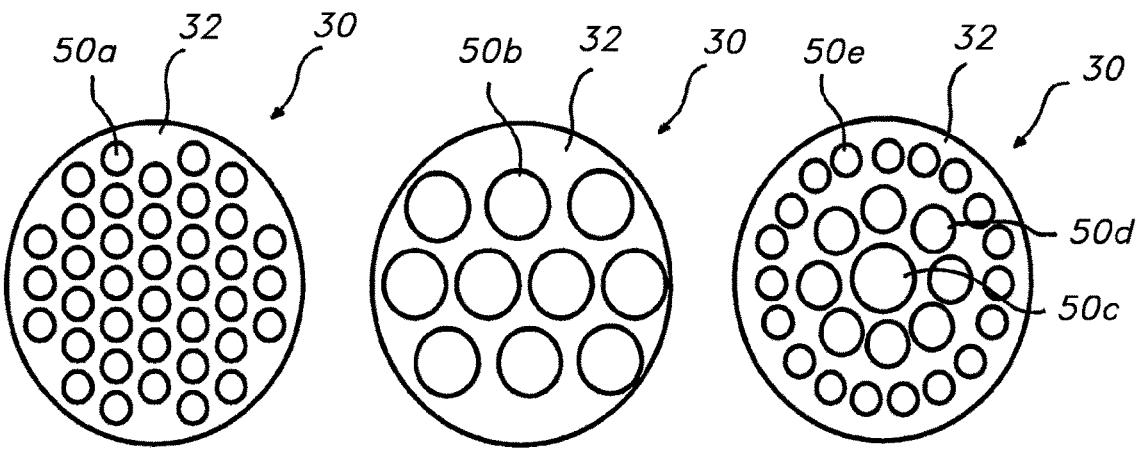
FIG. 3  FIG. 4  FIG. 5
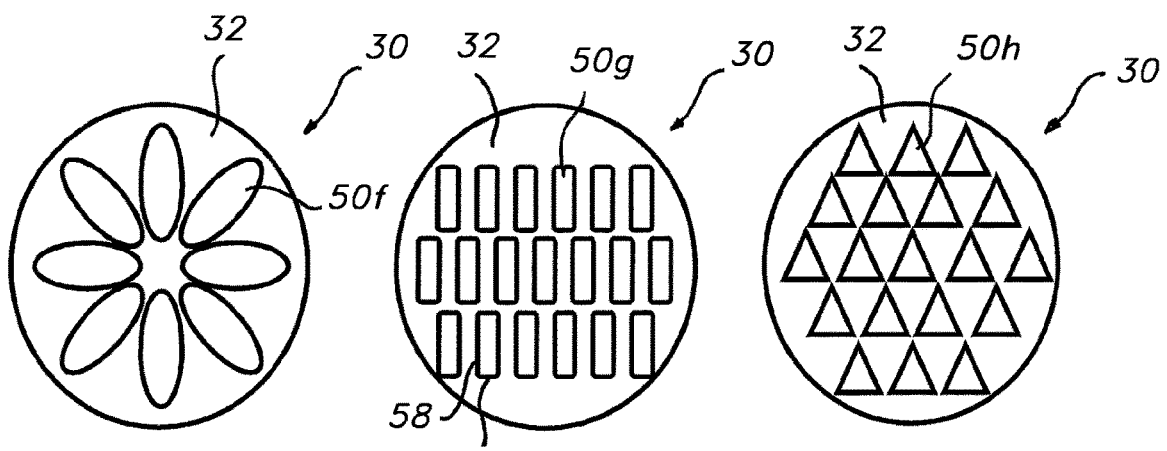
FIG. 6  FIG. 7  FIG. 8
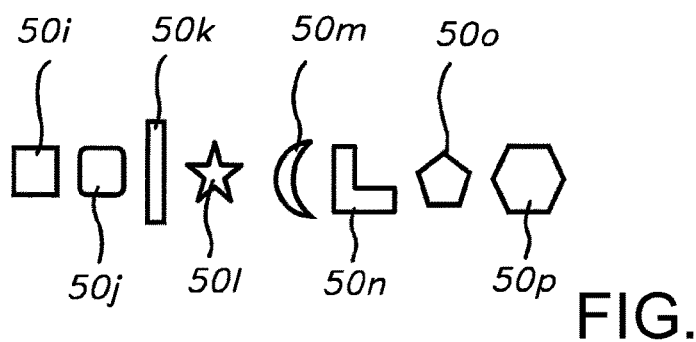
FIG. 9

TREATMENT HEAD FOR PERFORMING A MICRODERMABRASION PROCEDURE

This application is the U.S. National Phase application under 35 U.S.C. § 371 of International Application No. PCT/EP2015/072159 filed on Sep. 25, 2015, which claims the benefit of International Application No. 14186332.4 filed on Sep. 25, 2014. These applications are hereby incorporated by reference herein.

FIELD OF THE INVENTION

The present invention relates to a treatment head for performing a microdermabrasion procedure on a subject's skin. The present invention also relates to a skin care device for performing a microdermabrasion procedure on a subject's skin.

BACKGROUND OF THE INVENTION

Skin care devices are known for performing a microdermabrasion treatment on a subject's skin. Such skin care devices generally comprise a treatment head with abrasive elements, such as diamond particles, protruding from a treatment surface. The treatment head is applied to and moved over a subject's skin to remove skin particles, such as dead skin, from the subject's skin for skin resurfacing or rejuvenation.

DE 20 2014 102 546 describes a microdermabrasion device comprising a vacuum system and a device tip, wherein the vacuum system comprises a channel with a channel inlet at the device tip, wherein the channel inlet is surrounded by a channel rim, and wherein the device tip comprises a microdermabrasion zone configured remote from the channel inlet with a recession configured between the microdermabrasion zone and the channel rim.

U.S. Pat. No. 6,241,739 B1 describes a treatment tool and tissue collection system, for remove of outer layers of skin to provide a revitalized, fresh skin surface, and a method of using same, comprising an abrasive tipped tool mounted on the end of a tube, said tube being connected to a source of vacuum. The vacuum aids in maintaining intimate contact between the abrasive tip and the skin during the treatment process and transports the removed tissue to a collection container.

U.S. Pat. No. 6,299,620 B1 describes a system for atraumatic removal of skin surface layers in a treatment to induce neocollagenesis in the dermis to reduce wrinkles and alter the architecture of the dermal layers. A preferred embodiment of the system comprises (i) a hand-held instrument with a resilient working skin interface that carries microscopic diamond fragments for abrading the skin surface in a controlled manner; (ii) a fluid source for supplying sterile fluids to the skin interface for cleaning skin debris from the skin interface; and (iii) a negative pressure source for pulling fluid to the skin interface and thereafter aspirating fluid and skin debris from a treatment site. The skin interface is formed of a resilient material such as silicone to allow the working end to flex and atraumatically engage the skin surface as it is translated across a treatment site. The system also carries a disposable cartridge filled with fluid in the hand-held instrument.

SUMMARY OF THE INVENTION

It has been found that it is difficult to reliably manufacture these treatment heads, and so may lead to irritation of the subject's skin, or insufficient abrasion to provide an effective treatment.

It is an object of the invention to provide a treatment head and/or a skin care device which substantially alleviates or overcomes the problems mentioned above.

The invention is defined by the independent claim; the dependent claims define advantageous embodiments.

According to one aspect of the present invention, there is provided a treatment head, especially for performing a microdermabrasion procedure on a subject's skin, comprising a skin contact surface which is positionable against the subject's skin, and at least one vacuum aperture at the skin contact surface, the at least one vacuum aperture defining a path at which a vacuum is generatable, wherein the at least one vacuum aperture has an abrasive edge defined by a juncture of the vacuum aperture and the skin contact surface, the abrasive edge being configured to act on the subject's skin. Hence, the treatment head may especially be used in a microdermabrasion procedure on a subject's skin.

With this arrangement it is possible to draw the subject's skin against the abrasive edge. Furthermore, during manufacture it is possible accurately control the abrasive properties of the treatment head.

Furthermore, it has been found that the provision of a vacuum aperture at which a vacuum is generated together with an abrasive edge at the juncture of the vacuum aperture provides a synergistic effect to maximise the efficiency of the microdermabrasion procedure provided by the treatment head on the subject's skin.

The at least one vacuum aperture may comprise a sidewall. The abrasive edge may be defined by the juncture of the sidewall and the skin contact surface.

Therefore, ease of manufacture of the abrasive edge is maximised. Especially, the vacuum apertures are (thus) configured as abrasive elements. Furthermore, it is possible to form a skin contact surface (substantially) without any abrasive elements protruding from the skin contact surface. This helps to maximise movement of the treatment head over the subject's skin when the skin contact surface is positioned against and urged over the subject's skin. Hence, the skin contact surface may substantially not comprise abrasive elements (such as diamond particles) protruding from the skin contact surface. Hence, in embodiments the skin contact surface comprises substantially no abrasive elements protruding from the skin contact surface.

The abrasive edge may be defined around the periphery of the at least one vacuum aperture.

With this arrangement, the abrasive edge is able to provide an abrading action of a skin of the user, irrespective of the direction in which the treatment head is moved over the subject's skin when the skin contact surface is in contact with the subject's skin.

The abrasive edge may have a radius. Especially, the radius is equal to or smaller than 50 µm, such as equal to or smaller than 40 µm, even more especially equal to or smaller than 30 µm, such as smaller than 20 µm, like in the range of 30-0.5 µm. The abrasive edge may have a right angle or an obtuse angle or an acute angle. Especially, the angle is equal to or smaller than 135°, especially equal to or smaller than 90°.

Therefore, it is possible to control the abrasive effect provided by the abrasive edge. It is possible to ensure that the abrasive effect of the abrasive edge is restricted from causing irritation of the subject's skin.

The at least one vacuum aperture may have a minor axis of between 0.5 mm and 5 mm. Especially, all vacuum apertures have a minor axis of between 0.5 mm and 5 mm. When the vacuum apertures have a circular cross-section, the minor axis equals to the diameter.

With this arrangement it is possible to control doming of the user's skin into the at least one vacuum aperture. This helps to control the abrasive action provided by the abrasive edge.

The abrasive edge may comprise a first section and a second section, wherein the second section is configured to provide a different action on the skin to the first section. With this arrangement it is possible for different treatment actions to be applied to the subject's skin in dependence on the direction in which the treatment head is moved over the subject's skin. For example, with an elongate vacuum aperture different doming of the subject's skin may occur dependent on the direction of movement of the treatment head over the subject's skin.

The treatment head may comprise an array of spaced vacuum apertures.

Therefore, it is possible to ensure that an array of abrasive edges are provided at the skin contact surface. This helps to maximise the efficiency of the treatment applied by the treatment head. Furthermore, this allows an abrasive action to be provided across the skin contact surface.

The treatment head may include at least two vacuum apertures, such as at least eight, like at least ten, such as at least 28, or even more, such as at least 38, or yet even more.

The skin contact surface may have a surface roughness Ra between 1 μm and 15 μm. For instance, the skin contact surface does not include an abrasive coating. This means that the skin contact surface is able to glide over the subject's skin when the skin contact surface is disposed against the subject's skin. This means that the skin contact surface itself does not act on the subject's skin and so is prevented from causing irritation of the subject's skin. This also helps to minimise the effort required for a user, which may be the subject, to move the treatment head over the subject's skin. Hence, the skin contact surface is configured to glide over the subject's skin, during use of the device, without substantially having abrasive effect. The abrasive effect is substantially only due to contact of the subject's skin, during use of the device, with the abrasive edges.

The skin contact surface may be planar. Therefore, the skin contact surface may be easily manufactured.

At least part of the skin contact surface may have a convex shape. This helps to ensure that a correct orientation of the skin contact surface in contact with the subject's skin is achieved. Furthermore, this aids gliding of the treatment head over the subject's skin, and so minimising pulling of the subject's skin.

According to another aspect of the present invention, there is provided a skin care device for performing a microdermabrasion procedure on a subject's skin comprising a treatment head as described herein.

The skin care device may comprise a vacuum generator configured to generate a vacuum at the at least one vacuum aperture.

Therefore, it is possibly to simply provide a negative pressure at the at least one vacuum aperture.

The skin care device may further comprise a vacuum passage communicating the vacuum generator with a vacuum outlet of the at least one vacuum aperture.

With this arrangement it is possible to simply provide a negative pressure at the at least one vacuum aperture.

The vacuum generator may be configured to generate a vacuum at the at least one vacuum aperture equal to or greater than 15 kPa.

This means that efficiency of the microdermabrasion treatment provided by the treatment head may be maximised. It has been surprisingly found that when no or a minimal vacuum action is provided at the at least one vacuum aperture that no abrasive action is provided by the abrasive edge.

The skin care device may further comprise a positive pressure generator. The treatment head may comprise at least one positive pressure aperture, and the skin care device may be configured to provide a positive pressure at the at least one positive pressure aperture. With this arrangement it is possible to maximise the handling of the skin care device as it is moved over the subject's skin. It is possible to enhance the gliding experience of the treatment head over the subject's skin. The application of a positive pressure at the at least one positive pressure aperture may provide a massaging effect to the subject's skin to enhance the treatment.

The skin care device may comprise a body wherein the treatment head is removable from the body. Therefore, in such embodiments the treatment head is interchangeable with another treatment head.

With this arrangement it is possible to remove the treatment head to aid cleaning. Furthermore, it is also possible to change a worn treatment head with a new treatment head. Treatment heads with different configurations and therefore different treatment characteristics may also be interchangeably used.

Hence, the invention also provides a kit of parts including such body and one or more, especially a plurality of treatment heads that are removably connectable with the body (with an attachment arrangement), to provide the herein described skin care device. When a plurality of treatments heads is comprised by the kit of parts, optionally two or more different treatment heads (having different treatment characteristics) may be comprised by the kit.

The skin care device is especially not configured to provide free flowing abrasive particles.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which:

FIG. 3 is an illustrative plan view of one embodiment of the treatment head showing one arrangement of an array of vacuum apertures;

FIG. 4 is an illustrative plan view of one embodiment of the treatment head showing another arrangement of an array of vacuum apertures;

FIG. 5 is an illustrative plan view of one embodiment of the treatment head showing another arrangement of an array of vacuum apertures;

FIG. 6 is an illustrative plan view of one embodiment of the treatment head showing another arrangement of an array of vacuum apertures;

FIG. 7 is an illustrative plan view of one embodiment of the treatment head showing another arrangement of an array of vacuum apertures;

FIG. 8 is an illustrative plan view of one embodiment of the treatment head showing another arrangement of an array of vacuum apertures;

FIG. 9 is an illustrative plan view of different profiles of vacuum apertures;

The schematic drawings are not necessarily to scale.

DETAILED DESCRIPTION OF EMBODIMENTS

Figure 1:
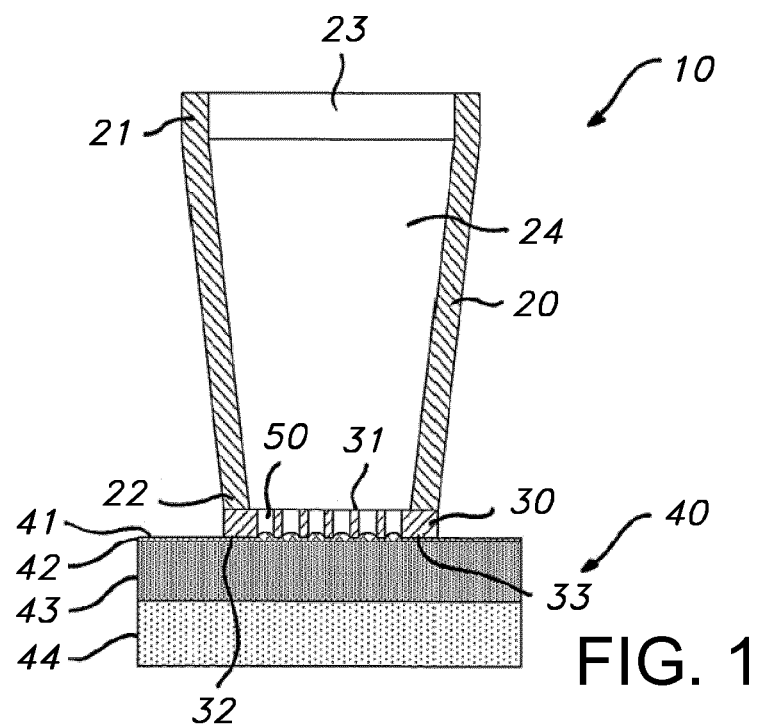
FIG. 1 is an illustrative cross-sectional side view of an embodiment of a skin care device having a treatment head for performing a microdermabrasion procedure positioned against a subject's skin.
Figure 2:
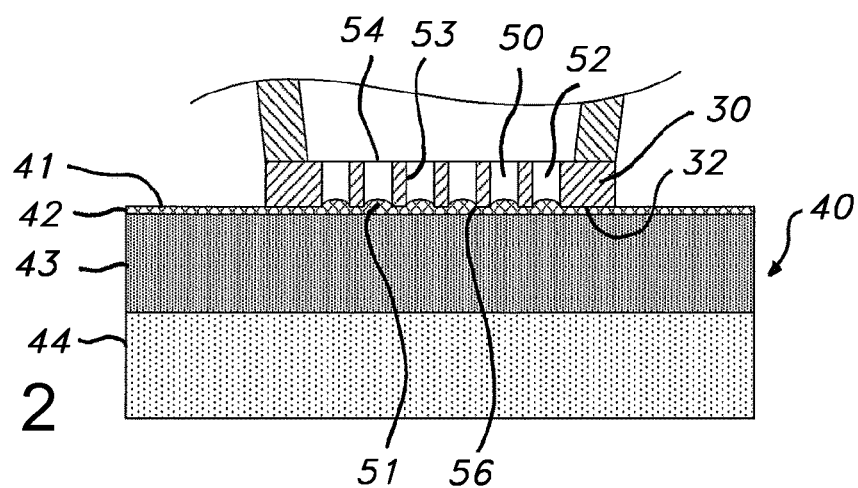
FIG. 2 is an illustrative cross-sectional side view of part of the embodiment of the skin care device shown in FIG. 1 positioned against a subject's skin.

A skin care device 10 for performing a microdermabrasion skincare procedure on a subject is shown in FIGS. 1 and 2. The skin care device 10 has a body 20 and a treatment head 30. The body 20 is elongate and defines a handle portion 21. A treatment end 22 is defined at one end of the skin care device 10. The handle portion 21 enables a user to hold and manoeuvre the device 10 and to position the treatment end 22 against a subject's skin 40.

A subject's skin 40 comprises a skin surface 41 formed by a stratum corneum layer 42, an epidermis layer 43 below the stratum corneum layer 42 and a dermis layer 44 below the epidermis layer 43. The treatment head 30 is configured to act on the skin surface 41 to remove skin particles, such as dead skin, from the skin surface 41 and to act on the stratum corneum layer 42 to remove part of the stratum corneum layer 42.

The treatment head 30 is at the treatment end 22 of the skin care device 10. The treatment head 30 is removably mounted to the body 20. The treatment head 30 is mounted to the body 20 by an attachment arrangement (not shown). The attachment arrangement is conventional and so a detailed description will be omitted but may, for example, be a threaded arrangement. A rear side 31 of the treatment head 30 mounts to the body 20. A fluid seal is formed between the body 20 and the treatment head 30 when the treatment head 30 is mounted to the body 20. The fluid seal extends around the periphery of the treatment head 30.

The treatment head 30 is removeably mounted to the body 20 to aid cleaning or replacement of the treatment head 30. By removably mounting the treatment head 30 with the body 20 it is possible for the body 20 to be used interchangeably with different treatment heads, for example treatment heads with different configurations and therefore different characteristics may also be interchangeably used. Alternatively, the treatment head 30 may be fixedly mounted to the body 20, such that it is not removable. This may help simplify construction of the skin care device 10.

The skin care device 10 has a vacuum generator 23, acting as an air flow generator. The vacuum generator 23 is configured to produce a negative pressure. The vacuum generator 23 is in the body 20. A vacuum passage 24 is defined in the body 20. The vacuum passage 24 fluidly communicates the vacuum generator 23 with the treatment head 30. The rear side 31 of the treatment head 30 defines one end of the vacuum passage 24. The vacuum generator 23 is configured to generate a negative pressure in the vacuum passage 24.

The skin care device 10 further comprises a power supply (not shown) and a user input (not shown) for controlling operation of the skin care device 10. The power supply is a rechargeable battery, however it will be understood that alternative power supply arrangements may be used, such as a mains power supply. The user input is a switch which is operable to actuate the vacuum generator 23. However, the user input may control other functions of the skin care device.

The treatment head 30 in the present embodiment is generally disc shaped, although alternative configurations are envisaged. That is, the treatment head 30 is generally cylindrical.

The treatment head 30 has a skin contact surface 32. The skin contact surface 32 is defined on an exposed side 33 of the treatment head 30. The exposed side 33 of the treatment head 30 is an opposing side of the treatment head 30 to the rear side 31. The skin contact surface 32 is planar. However, alternative arrangements are envisaged. For example, the skin contact surface 32 may be domed as will be described hereinafter. The skin contact surface 32 is smooth. That is, the skin contact surface 32 is configured to glide over the subject's skin 40 when the skin contact surface 32 is disposed there against, as shown in FIGS. 1 and 2. The surface roughness Ra of the skin contact surface 32 is especially between 1 μm and 15 μm. This means that the skin contact surface 32 of the treatment head 30 is able to glide over the skin surface 41 of the subject's skin 40 when the skin contact surface 32 is disposed against the subject's skin 40. This means that the skin contact surface 32 itself does not (substantially) act (abrasively) on the subject's skin 40 and so is prevented from causing irritation of the subject's skin 40. This also helps to minimise the effort required for a user, which may be the subject, to move the treatment head 30 over the subject's skin 40 without pulling on the subject's skin 40.

The treatment head 30 is formed from aluminum. However, the treatment head 30 may be formed from alternative materials, such as a ceramic, glass, sapphire, or a plastic. The treatment head 30 may have a coating (not shown) forming the skin contact surface 32.

The treatment head 30 has an array of vacuum apertures 50. The vacuum apertures 50 are at the skin contact surface 32. The vacuum apertures 50 communicate with the skin contact surface 32. That is, each vacuum aperture 50 has an opening forming a vacuum inlet 51 at the skin contact surface 32. The vacuum apertures 50 extend from the skin contact surface 32. Each vacuum aperture 50 defines a vacuum path 52 at which a vacuum is generatable when the vacuum aperture 50 is disposed at the subject's skin 40. Each vacuum aperture 50 has a sidewall 53. The sidewall 53 extends from the vacuum inlet 51 to a vacuum outlet 54 at the rear side 31 of the treatment head 30.

Each vacuum aperture 50 extends through the treatment head 30. Therefore, vacuum paths 52 are formed through the treatment head 30 from the skin contact surface 32. An abrasive edge 56 is defined at the vacuum inlet 51 of each vacuum aperture 50. The abrasive edge 56 is formed at the juncture of the sidewall 53 of the vacuum aperture 50 and the skin contact surface 32. The abrasive edge 56 extends around the periphery of the vacuum inlet 51. In the present embodiment, the vacuum inlet 51 is circular. The abrasive edge 56 extends circumferentially around the vacuum inlet 51.

The abrasive edge 56 is formed at the juncture of the sidewall 53 of the vacuum aperture 50 and the skin contact surface 32. The abrasive edge 56 is on the plane of the skin contact surface 32. The abrasive edge 56 does not (substantially) protrude from the skin contact surface 32. In the present embodiment, the sidewall 53 extends perpendicular to the skin contact surface 32. Therefore, the abrasive edge 56 is formed by the right angled juncture between the sidewall 53 and the skin contact surface 32. However, it will be understood that the angles of the faces forming the abrasive edge 56 may vary.

Figure 10:
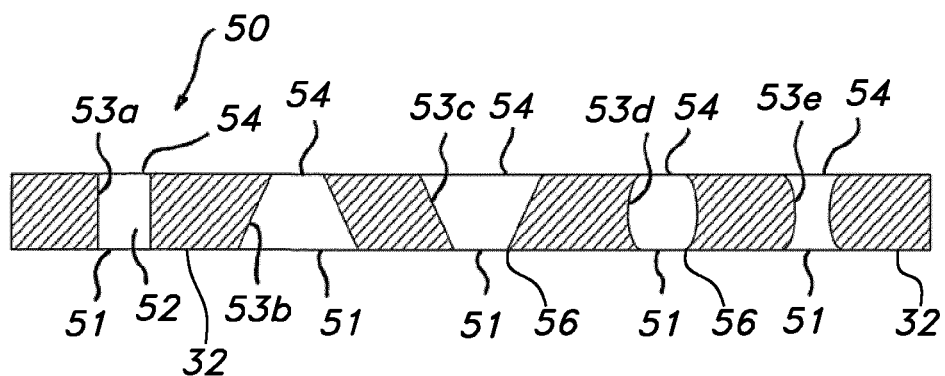
FIG. 10 is an illustrative cross sectional side view of different sidewall configurations of the vacuum apertures.

In the present embodiment, the abrasive edge 56 is formed by two faces, the sidewall 53 and skin contact surface 32, adjoining each other. However, it will be understood that the juncture forming the abrasive edge 56 may comprise a radius or a bevel. Therefore, the sharpness of the juncture between the sidewall 53 and skin contact surface 32 may be controlled, and reduced if necessary. This allows for the level of abrasiveness of the abrasive edge 56 to be accurately determined during manufacture. It will also be understood that the level of abrasiveness of the abrasive edge 56 may be determined in part based on the material used to form the treatment head 30. It will be understood that the cross-sectional profile of the sidewall 53 may vary. In the present embodiment, the sidewall 53 has a linear cross-sectional profile. In such an arrangement, the cross-sectional area of the vacuum aperture 50 is constant along the vacuum path 52 defined between the vacuum inlet 51 and vacuum outlet 54. Alternative exemplary cross-sectional profiles are shown in FIG. 10. The present embodiment of sidewall, represented by reference numeral 53a, is also shown. In another embodiment, the sidewall 53b has a converging cross-sectional profile from the vacuum inlet 51 to the vacuum outlet 54. In another embodiment, the sidewall 53c has a diverging cross-sectional profile from the vacuum inlet 51 to the vacuum outlet 54. In another embodiment, the sidewall 53d has a concave cross-sectional profile. In another embodiment, the sidewall 53e has a convex cross-sectional profile.

The treatment head 30 comprises the array of vacuum apertures 50. Such an arrangement is shown in FIG. 3. The vacuum apertures 50a shown in FIG. 3 have a circular profile. In this arrangement, the vacuum apertures 50a are evenly spaced from each other. Thirty eight vacuum apertures 50a are shown, however it will be understood that the number, arrangement and shape of the vacuum apertures 50a may vary. Each vacuum aperture 50a has a diameter of 1 mm. However, it will be understood that in another arrangement, the diameter of the vacuum apertures 50a may differ.

Referring to FIG. 4, another arrangement of the array of vacuum apertures 50b is shown. In this embodiment, seven vacuum apertures 50b are formed in the skin contact surface 32. These vacuum apertures 50b have a greater diameter than those shown in FIG. 3.

Comparing FIGS. 3 and 4, the latter may be applied for a more harsh microdermabrasion procedure and the former may be applied for a more sensitive microdermabrasion procedure.

Referring to FIG. 5, another arrangement of the array of vacuum apertures 50c, 50d, 50e is shown. In this embodiment, three different sets of vacuum apertures 50c, 50d, 50e are shown. A first set is defined by a single vacuum aperture 50c. The single vacuum aperture 50c is disposed on the central axis of the treatment head 30. The single vacuum aperture 50c has a diameter of 2 mm. A second set is defined by an array of eight vacuum apertures 50d extending circumferentially around the single vacuum aperture 50c. Each of the vacuum apertures 50d of the second set has a diameter of 1 mm. A third set is defined by an array of nineteen vacuum apertures 50e extending circumferentially around the second set of vacuum apertures 50d. Each of the vacuum apertures 50e of the third set has a diameter of 0.5 mm. With this arrangement, it is possible to provide a range of abrasive actions applied by one treatment head 30.

Referring to FIG. 5, such treatment head 30 may be applied for a relatively strong abrasion in the middle, preceded and followed by a gentle polishing at the edge. Referring to FIG. 6, another arrangement of the array of vacuum apertures 50f is shown. In this embodiment, eight vacuum apertures 50f form the array and are arranged in a radially extending arrangement. Each of the array of vacuum apertures 50f has an elliptical shape. The major axis dimension, that is length, is 4.5 mm and the minor axis dimension, that is width, is 1.5 mm.

Referring to FIG. 7, another arrangement of the array of vacuum apertures 50g is shown. In this embodiment, nineteen vacuum apertures 50g form the array. In this embodiment, each of the array of vacuum apertures 50g has a rectangular shape. The major axis dimension, that is length, is 3 mm and the minor axis dimension, that is width, is 1 mm.

Referring to FIG. 7, such treatment head 30 may especially be applied for providing a relatively strong or harsh microdermabrasion in a first direction (here left to right or vice versa) and a more gentle microdermabrasion in a second direction (here up or down).

Referring to FIG. 8, another arrangement of the array of vacuum apertures 50h is shown. In this embodiment, nineteen vacuum apertures 50h form the array. In this embodiment, each of the array of vacuum apertures 50h has a triangular shape.

Referring to FIG. 9, further profile shapes of the vacuum apertures 50 are shown. It will be understood that each profile shape may be used in combination with another profile shape to form an array of vacuum apertures 50. Such profile shapes of the vacuum apertures 50, that may be used in the treatment head 30 include, but are not limited to, circular shaped vacuum apertures 50a, 50b, 50c, 50d, 50e as shown in FIGS. 3 to 5, elliptical shaped vacuum apertures 50f as shown in FIG. 6, rectangular shaped vacuum apertures 50g as shown in FIG. 7, triangular shaped vacuum apertures 50h as shown in FIG. 8, square shaped vacuum apertures 50i, filleted square shaped vacuum apertures 50j, slit shaped vacuum apertures 50k, star shaped vacuum apertures 50l, crescent shaped vacuum apertures 50m, L-shaped vacuum apertures 50n, pentagonal shaped vacuum apertures 50o, and hexagonal shaped vacuum apertures 50p.

In the present arrangement, the vacuum apertures 50 generally have a maximum minor axis dimension of between 0.5 mm and 5 mm. That is, the maximum width of each vacuum aperture 50. For example, in FIG. 6, the major axis dimension, that is length, is 4.5 mm and the minor axis dimension is 1.5 mm. By providing a maximum minor axis dimension it is possible to restrict the doming of the subject's skin in each vacuum aperture 50 and so maximise the effective treatment applied by the treatment head 30 during use.

It has been found that vacuum apertures 50 having an elongate configuration are able to provide different treatment effects dependent on the direction in which the treatment head 30 is moved over the subject's skin. For example, referring to FIG. 7, each of the array of vacuum apertures 50g has a rectangular shape. This provides the abrasive edge 56 with a first section 57 and a second section 58. With such an elongate vacuum aperture different doming of the subject's skin has been found to occur when the treatment head 30 is moved in a direction transverse to the first section 57 compared to when moved in a direction transverse to the second section 58. When moved in a direction transverse to the second section 58 an increased abrasive action acts on the subject's skin. Although the vacuum apertures 50g having this effect are shown in FIG. 7 as rectangular, it will be understood that alternative shapes may provide the same effect.

Operation of the skin care device 10 will now be described with reference to FIGS. 1 and 2. To operate the skin care device 10, the vacuum generator 23 is actuated to generate a negative pressure in the vacuum passage 24. This causes an airflow through the array of vacuum apertures 50.

A user, which may be the subject being treated or someone performing the treatment on the subject, orientates and positions the treatment end 22 of the skin care device 10 against the skin surface 41 of the subject's skin 40. Therefore, the skin contact surface 32 is brought into contact with the subject's skin 40. As there are no protrusions, such as abrasive elements, protruding from the skin contact surface 32 a seal is formed between the skin surface 41 and the vacuum apertures 50.

A vacuum is generated at the vacuum inlet 51 of the vacuum apertures 50 due to the reduction in pressure formed in the vacuum passage 24. Therefore, skin 40 at the vacuum inlet 51 of each vacuum aperture 50 is urged to distend slightly through the vacuum inlet 51. This causes a slight doming of the subject's skin 40 at each vacuum inlet 51. When the treatment head 30 is drawn over the subject's skin 40, by the user moving the skin care device 10 over the subject's skin 40, the skin contact surface 32 moves relative to the subject's skin 40. The abrasive edge 56 of each vacuum aperture 50 is moved over the subject's skin 40 and acts on the subject's skin 40. It has been surprisingly found that without a vacuum being generated in the vacuum apertures 50, an abrasive action of the abrasive edge 56 on skin does not occur. When a negative pressure is applied at each of the vacuum apertures 50 the corresponding abrasive edge 56 acts on the subject's skin 40 and acts to remove part of the skin surface 41. As the abrasive edge 56 extends around the periphery of the vacuum aperture 50, an abrasive action is performed irrespective of the direction of movement of the treatment head 30 over the subject's skin 40.

The slight doming of the subject's skin 40 at each of the vacuum apertures 50 acts to enhance the abrasive action performed on the subject's skin 40 by the vacuum aperture 50. The restriction caused by the restricted width of each vacuum aperture 50 acts to prevent excessive doming and so an excessive abrasive action of the subject's skin. This helps to prevent discomfort and irritation. The vacuum generated at the vacuum inlet 51 by the vacuum generator 23 is equal to or greater than 15 kPa.

It will be understood that the abrasive action is dependent on, for example, the size of each vacuum aperture 50, the shape of each vacuum aperture 50, and the configuration of the abrasive edge 56.

Figure 11:
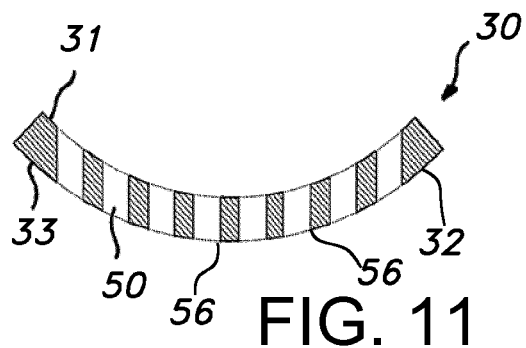
FIG. 11 is an illustrative cross-sectional side view of one embodiment of the treatment head shown in FIG. 1.
Figure 12:
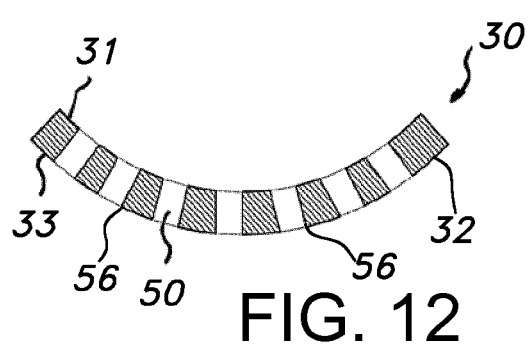
FIG. 12 is an illustrative schematic cross-sectional side view of one embodiment of the treatment head shown in FIG. 1.

Although in the above described embodiments the skin contact surface 32 is planar, it will be understood that alternative arrangements of the skin contact surface 32 are envisaged. Another embodiment of the treatment head 30 is shown in FIG. 11. In this embodiment, the skin contact surface 32 is domed. That is, the skin contact surface 32 has a convex shape. In this embodiment, the vacuum apertures 50 extend parallel to each other through the treatment head 30 between the exposed side 33 and the rear side 31 of the treatment head 30. In an alternative arrangement shown in FIG. 12 the vacuum apertures 50 extend radially through the treatment head 30 between the exposed side 33 and the rear side 31 of the treatment head 30. The domed shape of the skin contact surface 32 helps to ensure that a correct orientation of the treatment head 30 is maintained. By providing radially aligned vacuum apertures 50 it is possible for consistent abrasive action to be performed by each abrasive edge 56 of each vacuum aperture 50. In an alternative embodiment, the skin contact surface 32 defines a recess. That is, the skin contact surface 32 has a concave shape.

Figure 13:
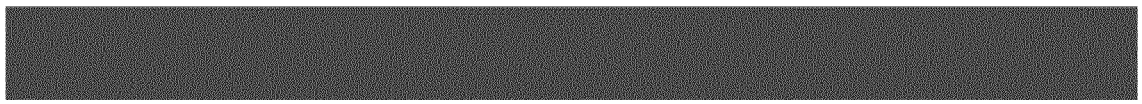
FIG. 13 is an illustrative schematic cross-sectional side view of another embodiment of a skin care device having a treatment head for performing a microdermabrasion procedure positioned against a subject's skin.
Figure 13:
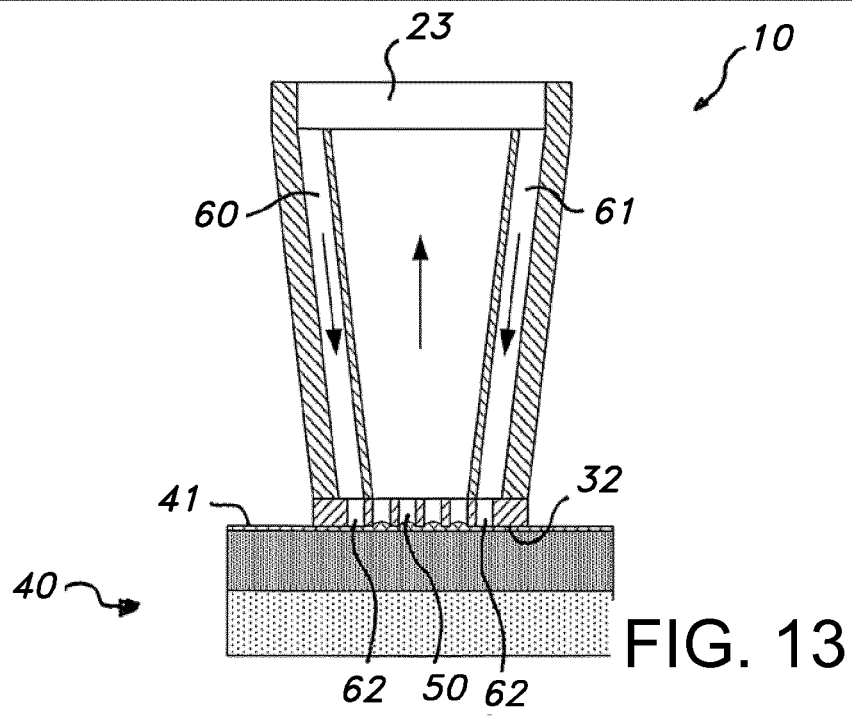

Referring now to FIG. 13, an alternative embodiment of the skin care device 10 is shown. It will be understood that the skin care device 10 shown in FIG. 13 is generally the same as the embodiments of skin care device 10 described above, and so a detailed description will be omitted. Reference numerals and features corresponding to reference numerals and features described above will be retained. Furthermore, it will be understood that the skin care device 10 described herein may be used with many of the configurations of treatment heads 30 described above. However, in this embodiment the skin care device 10 comprises a positive pressure arrangement 60 configured to apply a positive pressure at part of the treatment head 30.

The positive pressure arrangement 60 comprises a positive pressure passage 61 and an array of positive pressure apertures 62. In the present embodiment, the positive pressure is generated by a positive pressure generator which is integrally formed with the vacuum generator 23, acting as an air flow generator. However, it will be understood that the positive pressure generator and vacuum generator may be separate.

In the present arrangement, the positive pressure arrangement is configured to provide a positive pressure at the skin contact surface 32 proximate to the periphery of the skin contact surface 32. That is, the array of positive pressure apertures 62 are disposed circumferentially around the array of vacuum apertures 50. However, it will be understood that alternative arrangements are envisaged. The array of positive pressure apertures 62 are at the skin contact surface 32, and so are able to provide a positive pressure to the subject's skin during use. The configuration of each positive pressure aperture 62 is similar to the configuration of the vacuum apertures 50 described above and so a detailed description will be omitted herein.

During use of the skin care device 10 described above with reference to FIG. 13, a positive pressure is applied to the subject's skin 40 at each positive pressure aperture 62 when the skin contact surface 32 of the treatment head 30 is in contact with the subject's skin 40. The positive pressure urges the subject's skin 40 away from the skin contact surface 32. Therefore, handling of the device may be improved. The negative pressure applied to the subject's skin 40 draws the subject's skin 40 towards the skin contact surface 32. Therefore, the combined urging and drawing may cause a massaging effect on the skin to enhance microcirculation in the subject's skin 40.

Figure 14:
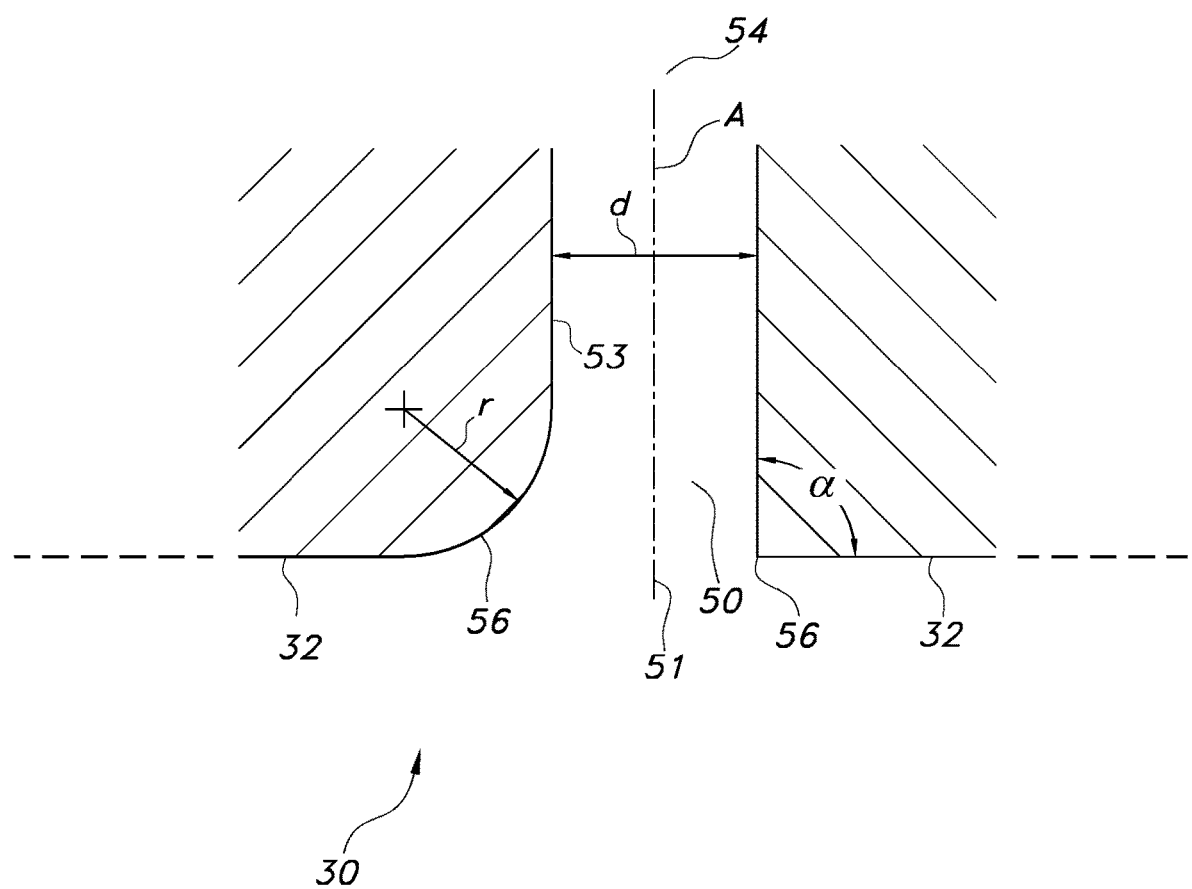
FIG. 14 is an illustrative cross sectional side view of to schematically depict some aspects of the vacuum apertures.

FIG. 14 is an illustrative cross sectional side view of to schematically depict some aspects of the vacuum apertures. Reference A indicates a channel axis. The channel axis is especially configured in the cross-sectional plane. By way of example, on the left side a abrasive edge 56 with a radius r is shown, whereas on the right side an abrasive edge with a right angle is shown. The angle is indicated with reference a, which is here by way of example 90°. The angle $\alpha$ is the angle between the junction of the vacuum aperture 50 and the skin contact surface 32, i.e. here between the sidewall 53 and the skin contact surface 32. The angle α and the radius especially relate to angles and radii within a cross-sectional plane, as shown with the cross-sectional view in FIG. 14; they especially do not refer to angles or radii in a plane perpendicular to the channel axis A. For instance, a curvature in such plane is e.g. indicated with a minor axis. Here, the minor axis is indicated with reference d, which is the diameter in a substantially cylindrical channel. Note that the minor axis may vary over the channel axis length (see e.g. some embodiments of the vacuum apertures 50 in FIG. 10. The radius r is especially not larger than 30 μm. It appears that best abrasive effects may be obtained with radii r equal to or below about 50 μm. The radius r is especially not larger than 30 μm. The abrasive edge 56 on the right has a radius substantially equal to 0 μm. Especially, the angle α is equal to or smaller than 135°, especially equal to or smaller than 90°.

In an experiment, three different treatment tips (treatment heads) were created with various hole (vacuum aperture) diameters. The number of holes is such chosen to have an equal coverage per treatment tip. The hole diameters differ between the tips, but do not differ on the tip (i.e. tips such as schematically depicted in FIGS. 3 and 4). The vacuum apertures (holes) were substantially round. The following tips were provided and tested:

| Tip (treatment head) number | Vacuum aperture diameter (mm) | Number of vacuum apertures | Percentage coverage |
|---|---|---|---|
| 1 | 0.5 | 180 | 20 |
| 2 | 1 | 45 | 20 |
| 3 | 1.5 | 20 | 20 |

These treatment heads were tested in relation to a device with such treatment head without vacuum and in relation to a commercially available microdermabrasion device. The vacuum of the commercially available microdermabrasion device was 25 kPa; the vacuum per vacuum aperture was 60 cm Hg (80 kPa). From the microdermabrasion data it appears that the treatment head as described herein can provide the same results as with a commercially available microdermabrasion device, but is much more flexible in tuning the desired microdermabrasion. If further also appears that applying no vacuum to the treatment heads does substantially not provide an abrasive effect. Hence, the combination of the vacuum apertures with abrasive functionality and the vacuum provides the microdermabrasion. Treatment head 3 was experienced to provide a more harsh abrasion whereas treatment head 1 was experienced to provide a more gentle abrasion.

It will be appreciated that the term "comprising" does not exclude other elements or steps and that the indefinite article "a" or "an" does not exclude a plurality. A single processor may fulfil the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A treatment head, comprising a skin contact surface which is positionable against a subject's skin, and at least two vacuum apertures on the skin contact surface configured as abrasive elements, the at least two vacuum apertures each defining a vacuum path at which a vacuum is generatable, wherein the at least two vacuum apertures have an abrasive edge defined by a juncture of a sidewall of the vacuum aperture and the skin contact surface, wherein the abrasive edge extends around the periphery of a vacuum inlet along said juncture, the abrasive edge being configured to act on the subject's skin, wherein the sidewall has a convex cross-sectional profile extending along an entire length of the sidewall from an exposed side to a rear side, and wherein the at least two vacuum apertures have a maximum minor axis dimension of between 0.5 mm and 5 mm.

2. The treatment head according to claim 1, wherein the abrasive edge is defined around the periphery of the at least two vacuum apertures.

3. The treatment head according to claim 1, wherein the abrasive edge has a radius (r) equal to or smaller than 30 μm.

4. The treatment head according to claim 1, wherein the abrasive edge comprises a first section and a second section, wherein the second section is configured to provide a different action on the skin to the first section.

5. The treatment head according to claim 1, wherein the at least two vacuum apertures further comprise an array of spaced vacuum apertures.

6. The treatment head according to claim 1, wherein the skin contact surface has a surface roughness Ra between 1 µm and 15 µm.

7. The treatment head according to claim 1, wherein the skin contact surface is planar.

8. The treatment head according to claim 1, wherein at least part of the skin contact surface has a convex shape.

9. A skin care device comprising a treatment head according to claim 1.

10. The skin care device according to claim 9, comprising a vacuum generator configured to generate a vacuum at the at least two vacuum apertures.

11. The skin care device according to claim 10, further comprising a vacuum passage communicating the vacuum generator with a vacuum outlet of the at least two vacuum apertures.

12. The skin care device according to claim 9, further comprising a positive pressure generator, wherein the treatment head comprises at least one positive pressure aperture, and the skin care device is configured to provide a positive pressure at the at least one positive pressure aperture.

13. The skin care device according to claim 9, further comprising a body, wherein the treatment head is removable from the body so that the treatment head is interchangeable with another treatment head.

14. The treatment head according to claim 1, wherein the abrasive elements do not protrude from the skin contact surface.

15. The treatment head according to claim 1, wherein the at least two vacuum apertures are disposed at or near a central axis of the treatment head.

16. The treatment head according to claim 1, wherein the sidewall extends from the vacuum inlet at the skin contract surface to a vacuum outlet at a rear side of the treatment head.

17. The treatment head according to claim 1, wherein the at least two vacuum apertures further comprise an array of spaced vacuum apertures having a circular profile, the vacuum apertures being evenly spaced from one another and having a diameter of at least 1 mm.

18. The treatment head according to claim 1, wherein the at least two vacuum apertures further comprise an array of spaced vacuum apertures arranged in a radially extending arrangement, the vacuum apertures having an elliptical shape having a major axis dimension of 4.5 mm and a minor axis dimension of 1.5 mm.

19. The treatment head according to claim 1, wherein the at least two vacuum apertures have a rectangular shape thereby providing the abrasive edge with a first section and a second section, the first section comprising two parallel sides of the rectangle and the second section comprising two further parallel sides of the rectangle, wherein the first section is configured to provide a different action on the skin to the second section in dependence upon a direction in which the treatment head is moved over the subject's skin.

20. The treatment head according to claim 19, wherein an increased abrasive action occurs on the subject's skin when the treatment head is moved in a direction transverse to the second section.

21. A treatment head, comprising a skin contact surface which is positionable against a subject's skin, and at least two vacuum apertures on the skin contact surface configured as abrasive elements, the at least two vacuum apertures defining a vacuum path at which a vacuum is generatable, wherein the at least two vacuum apertures have an abrasive edge defined by a juncture of a sidewall of the vacuum apertures and the skin contact surface, wherein the abrasive edge extends around the periphery of a vacuum inlet along said juncture, the abrasive edge being configured to act on the subject's skin, wherein the sidewall has a concave cross-sectional profile extending along the entire length of the sidewall from an exposed side to a rear side, and wherein the at least two vacuum apertures have a maximum minor axis dimension of between 0.5 mm and 5 mm.

22. A skin care device comprising a treatment head according to claim 21.

23. A treatment head, comprising a skin contact surface which is positionable against a subject's skin, and at least two vacuum apertures on the skin contact surface configured as abrasive elements, the at least two vacuum apertures defining a vacuum path at which a vacuum is generatable, wherein the at least two vacuum apertures have an abrasive edge defined by a juncture of a sidewall of the vacuum apertures and the skin contact surface, wherein the abrasive edge extends around the periphery of a vacuum inlet along said juncture, the abrasive edge being configured to act on the subject's skin, wherein the sidewall has a diverging cross-sectional profile extending along the entire length of the sidewall from an exposed side to a rear side, and wherein the at least two vacuum apertures have a maximum minor axis dimension of between 0.5 mm and 5 mm.

24. A skin care device comprising a treatment head according to claim 23.

25. A treatment head, comprising a skin contact surface which is positionable against a subject's skin, and at least two vacuum apertures on the skin contact surface configured as abrasive elements, the at least two vacuum apertures defining a vacuum path at which a vacuum is generatable, wherein the at least two vacuum apertures have an abrasive edge defined by a juncture of a sidewall of the vacuum aperture and the skin contact surface, wherein the abrasive edge extends around the periphery of a vacuum inlet along said juncture, the abrasive edge being configured to act on the subject's skin, wherein the sidewall has a converging cross-sectional profile extending along the entire length of the sidewall from an exposed side to a rear side, and wherein the at least two vacuum apertures have a maximum minor axis dimension of between 0.5 mm and 5 mm.

* * * * *